United States Patent
Houben et al.

(10) Patent No.: US 8,684,920 B2
(45) Date of Patent: Apr. 1, 2014

(54) CLASSIFICATION OF SEVERITY OF MEDICAL CONDITION BY WAVELET BASED MULTI-RESOLUTION ANALYSIS

(75) Inventors: Richard P. M. Houben, Lanaken (BE); Mark Ver Heyen, Mol (BE)

(73) Assignee: Medtronic, Inc., Minneapolis, MN (US)

( * ) Notice: Subject to any disclaimer, the term of this patent is extended or adjusted under 35 U.S.C. 154(b) by 1315 days.

(21) Appl. No.: 12/168,711

(22) Filed: Jul. 7, 2008

(65) Prior Publication Data

US 2010/0004515 A1  Jan. 7, 2010

(51) Int. Cl.
*A61B 5/00* (2006.01)

(52) U.S. Cl.
USPC ........................................................ 600/300

(58) Field of Classification Search
USPC ................ 607/2–28; 600/508–519, 300, 301
See application file for complete search history.

(56) References Cited

U.S. PATENT DOCUMENTS

| | | |
|---|---|---|
| 7,313,434 B2 | 12/2007 | Belalcazar |
| 2004/0172080 A1 | 9/2004 | Stadler |
| 2004/0210147 A1 | 10/2004 | Houben |
| 2007/0055151 A1* | 3/2007 | Shertukde et al. ............ 600/437 |
| 2007/0156061 A1 | 7/2007 | Hess |
| 2008/0024293 A1 | 1/2008 | Stylos |
| 2008/0161657 A1 | 7/2008 | Bullens |
| 2008/0161701 A1 | 7/2008 | Bullens |
| 2009/0275855 A1 | 11/2009 | Zielinski et al. |

OTHER PUBLICATIONS

Richard Houben et al., "Classification of Decompensation in Heart Failure by Wavelet based Multi-Resolution Analysis", Summary, Medtronic Bakken Research Center, Cardian Rhythm Disease Management, Clinical Outcomes, Research & Biometry.
Crouse, Matthew S.; "Wavelet-Based Statistical Signal Processing Using Hidden Markov Models"; IEEE Transactions on Signal Processing; vol. 46, No. 4, Apr. 4, 1998; pp. 886-902.
PCT International Search Report; PCT/US2009/049137.

* cited by examiner

*Primary Examiner* — Scott Getzow
(74) *Attorney, Agent, or Firm* — Michael J. Ostrom

(57) ABSTRACT

A system and method are provided for classifying the severity of a medical condition detected by a medical device using wavelet based multi-resolution analysis of biomedical signals. Biomedical signals are converted into a set of wavelet coefficients including scales of wavelet coefficients at different resolutions ranging from a finest scale to a coarsest scale. Features of the biomedical signal useful in diagnosing a biomedical condition are identified by determining whether corresponding identifying features appear in at least one of the plurality of scales of wavelet coefficients. The identifying features determined to appear in the various scales of wavelet coefficients are conditionally linked together and used to classify a degree of severity of a diagnosed biomedical condition based on the number of identifying features appearing in different scales of wavelet coefficients. In some embodiments, alerts can be generated based on the diagnosed degree of severity of the biomedical condition.

18 Claims, 8 Drawing Sheets

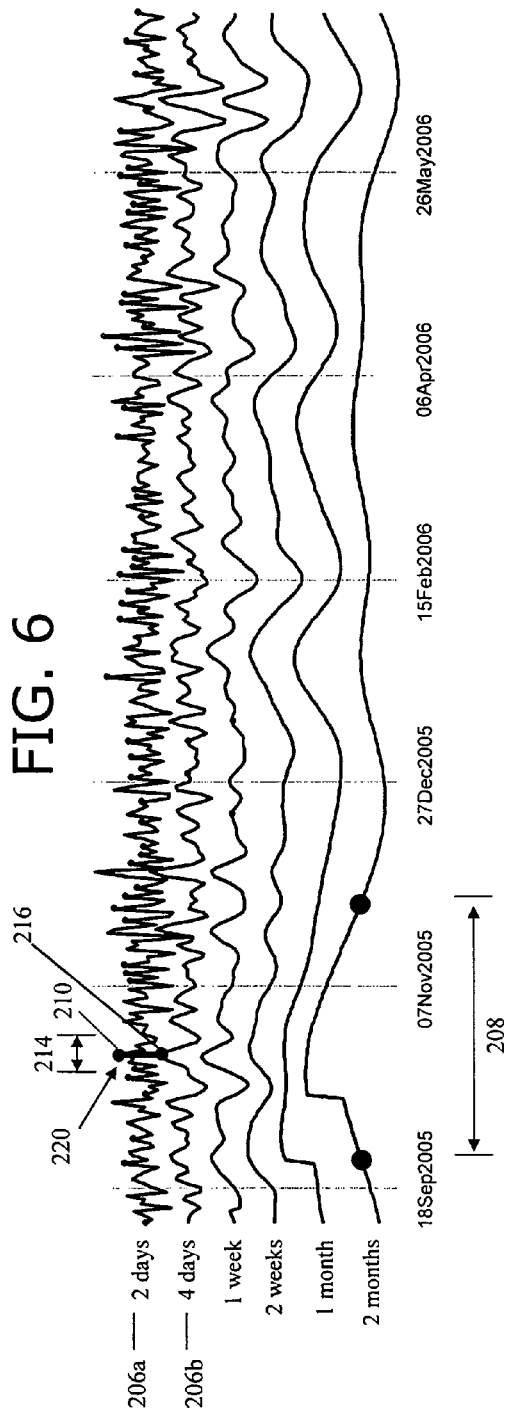
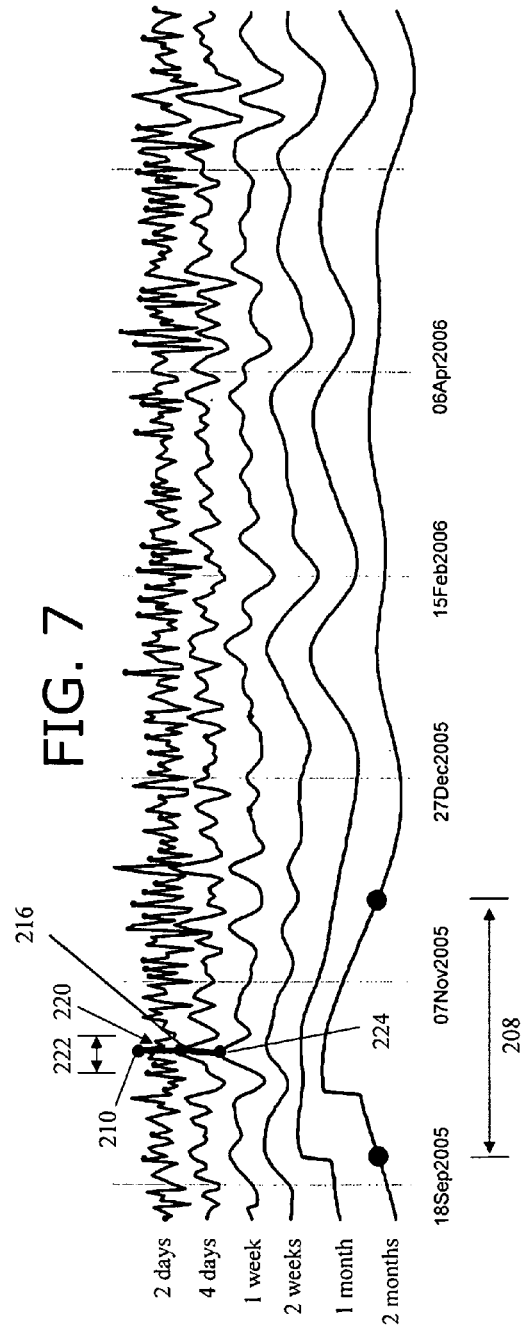

CLASSIFICATION OF SEVERITY OF MEDICAL CONDITION BY WAVELET BASED MULTI-RESOLUTION ANALYSIS

TECHNICAL FIELD

This disclosure relates generally to medical devices and more particularly to a system and method for classifying the severity of a medical condition detected by a medical device using wavelet based multi-resolution analysis performed on biomedical signals.

BACKGROUND

Early detection of the worsening of heart failure to prevent hospitalization is an ongoing challenge. Intra-thoracic impedance measurements can give a good indication of the fluid status of patients, with decreases in impedance being indicative of increases in fluid content and increases in impedance being indicative of decreases in fluid content. Knowledge of a patient's long-term impedance measurements and changes therein are a valuable clinical indicator of a patient's health.

The accumulation of fluid can indicate decompensation, failing heart circulation as well as several other conditions. There are several mechanisms or diseases that can cause or affect the accumulation of fluid. In general, fluid accumulation is a failure or over-response of the homeostatic process within the body. The body normally prevents the build up of fluids by maintaining adequate pressures and concentrations of salt and proteins and by actively removing excess fluid. Fluid accumulation can occur, for example, when the body's mechanisms for preventing fluid accumulation are affected by disease, such as heart failure, left-sided myocardial infarction, high blood pressure, altitude sickness, emphysema (all of which affect pressures), cancers that affect the lymphatic system, renal diseases, and diseases that disrupt the protein concentrations. Likewise, abnormally low fluid levels can also be problematic. As a result, providing an adequate monitor of the patient's fluid status can provide physicians and patients with a better tool to manage disease.

Determining the impedance values at which to notify a patient can prove difficult. On one hand, patients should be notified every time they are approaching a dangerously high or low fluid status. On the other hand, notifying patients when they face no dangerously high or low fluid status can result in the unnecessary consumption of time and resources. This can be especially problematic when the unnecessary consumption is multiplied over a large patient population.

SUMMARY

In one or more embodiments, a system and method are provided for classifying the severity of a medical condition detected by a medical device using wavelet based multi-resolution analysis. The method includes converting biomedical signal data into a set of wavelets, where the set of wavelet coefficients includes a plurality of scales of wavelet coefficients at different resolutions ranging from wavelet coefficients at a fine scale resolution to wavelet coefficients at a coarse scale resolution. In one or more embodiments, features of the biomedical signal useful in diagnosing a biomedical condition or parameter are identified by determining whether corresponding identifying features appear in at least one of the plurality of scales of wavelet coefficients. The identified features in each of the plurality of scales of wavelet coefficients are conditionally linked together and used to determine or classify a degree of severity of a biomedical condition based on the identified features of the biomedical signal. In one or more embodiments, features of the biomedical signal are identified by determining whether the magnitude of certain wavelet coefficients in certain scales of wavelet coefficients exceed predefined threshold values.

In one or more embodiments, it is initially determined whether an identified feature appears in wavelet coefficients at a first scale (e.g., the finest scale, the coarsest scale or a scale there between), where an identified featured appearing in wavelet coefficients at the first scale is selected as a base point for the conditional linking. The wavelet coefficients in an adjacent scale of wavelet coefficients is then analyzed to determine whether an identified feature appears in the adjacent scale of wavelet coefficients from the base point's scale within a first time period window surrounding the base point. In one or more embodiments, it is further determined whether the identified feature appearing in the adjacent scale of wavelet coefficients meets certain threshold criteria. If the certain threshold criteria are met, the identified feature is selected as a linking point and conditionally linked to the base point to represent a chain of conditional linking points.

In one or more embodiments, it is then determined whether an identified feature appears in another scale of wavelet coefficients adjacent to the scale for a selected one of the linking points in the chain of conditional linking points in a time period window surrounding the selected linking point. In some embodiments, the selected time period window surrounding the selected linking point from the chain of conditional linking points may vary from between scales of wavelet coefficients being analyzed. If an identified feature is located in the next adjacent scale of wavelet coefficients, it is determined whether the identified feature appearing in the next adjacent scale of wavelet coefficients meets certain threshold criteria. It is further determined whether the identified feature appearing in the next adjacent scale of wavelet coefficients is located within an overall time period window for the entire chain of conditional linking points. If both the threshold criteria and overall time period window conditions are satisfied, the identified feature is selected as a linking point and conditionally linked to the chain of conditional linking points having identified features appearing in the other scales of wavelet coefficients. In one or more embodiments, these various operations are repeated until a chain of conditional linking points has been completed from a starting base point. For example, the starting base point may be located at the finest scale so that the scale of wavelet coefficients gradually become coarser as the scales are analyzed, the starting base point may be located at the coarsest scale so that the scale of wavelet coefficients gradually become finer as the scales are analyzed, or the starting base point may be located at an intermediate scale of wavelet coefficients so that the scale of wavelet coefficients are analyzed in either a gradually finer direction, a gradually coarser direction or a combination of both directions. The chain of conditional linking points is complete if either an identified feature is not located in the next adjacent scale of wavelet coefficients, the certain threshold criteria are not satisfied for an identified feature in the next adjacent scale of wavelet coefficients, or the overall time period window condition is not satisfied for an identified feature in the next adjacent scale of wavelet coefficients.

In one or more embodiments, once the chain of conditional linking points has been determined, the degree of severity of the biomedical condition can be classified based on the number of linking points in the chain of conditional linking points. In one or more embodiments, the degree of severity of the biomedical condition can additionally or alternatively be classified based on whether the magnitude of certain wavelet coefficients in certain scales of wavelet coefficients exceed predefined threshold values. In some embodiments, an alert can be generated to at least one of the patient, a physician, and an emergency response team when certain degrees of severity of the biomedical condition are identified to exist.

In one or more embodiments, the identifying features appearing the scales of wavelet coefficients are peak wavelet coefficient values appearing within a selected period of time. By conditional linking of wavelet coefficient peaks into a chain extending between scales, the length of the chain can be associated with severity of the biomedical condition. In one or more embodiments, the biomedical condition to be classified includes decompensation in heart failure in a patient, where at least one of intra-thoracic impedance and intracardiac pressure values are used as the biomedical signal data. In this manner, the severity of heart decompensation in a patient can be easily detected and classified by wavelet transforming intra-thoracic impedance or intracardiac pressure values into multi-resolution scales of wavelet coefficients and conditionally linking the wavelet coefficient peaks.

In one or more embodiments, systems and devices are similarly disclosed for employing the methods for classifying the severity of a medical condition detected by a medical device using wavelet based multi-resolution analysis.

DRAWINGS

The above-mentioned features and objects of the present disclosure will become more apparent with reference to the following description taken in conjunction with the accompanying drawings wherein like reference numerals denote like elements and in which:

FIGS. 6 and 7 are further graphical illustrations of the set of wavelet coefficients of FIGS. 4 and 5 in accordance with the present disclosure.

DETAILED DESCRIPTION

The invention is directed to signal processing techniques for biomedical signals in which wavelet analysis is used. An biomedical signal can be represented by a finite set of wavelet coefficients which comprise a decomposition of the biomedical signal in the scale-time domain. In accordance with the invention, wavelet analysis techniques can be used to distinguish specific phenomena in biomedical signals. In particular, wavelet analysis can be used to classify the severity of a medical condition detected by a medical device using wavelet based multi-resolution analysis. Although many details of the invention are described in the context of particular types of biomedical signals, it is understood that the present teachings can be extended to any type of biomedical signal. For example, such wavelet analysis described herein may be performed on at least one of intra-thoracic impedance and intra-cardiac pressure signals in order to classify the severity of heart decompensation in a patient and generate appropriate responses. It is also understood that such wavelet analysis can be performed on electrograms or other types of signals to diagnose other types of biomedical conditions.

The wavelet transform enables decomposition of a biomedical signal into a set of wavelet coefficients at various scales (i.e., multi-resolution analysis). Generally, the wavelet transform converts the input biomedical signal into wavelet coefficients by correlating the input signals with a set of compressed and dilated wavelets that are generally derived from a single "mother" wavelet. At finer scales the wavelet transform is more sensitive to fine-grained details, whereas at coarser scales the long-term structure of the signal is emphasized. In one or more embodiments, a quadratic-spline wavelet is used to transform an intra-thoracic impedance signal into a set of wavelet coefficients, where the wavelet coefficient peaks represent the maximum negative slopes in the impedance signal. Wavelet coefficient maxima at coarser scales suggest a long-term negative impedance trend while short-term reduction of impedance exclusively produces peaks at finer scales. Severe decompensation in a patient is associated with a significant decrease of intra-thoracic impedance producing maxima at all scales of wavelet coefficients ranging from the finest scale to the coarsest scale. In contrast, moderate decompensation is confined to short-term impedance changes only generating maxima at finer scales. In one or more embodiments, a system and method are provided for conditional linking of wavelet coefficient peaks into a chain starting from the finest scale extending toward the coarsest scale in order to classify the severity of decompensation in a patient according to the length of the chain of conditionally linked wavelet coefficient peaks. The terms coarse scale and fine scale, however, are generally relative and can assume different values in different embodiments.

Figure 1:
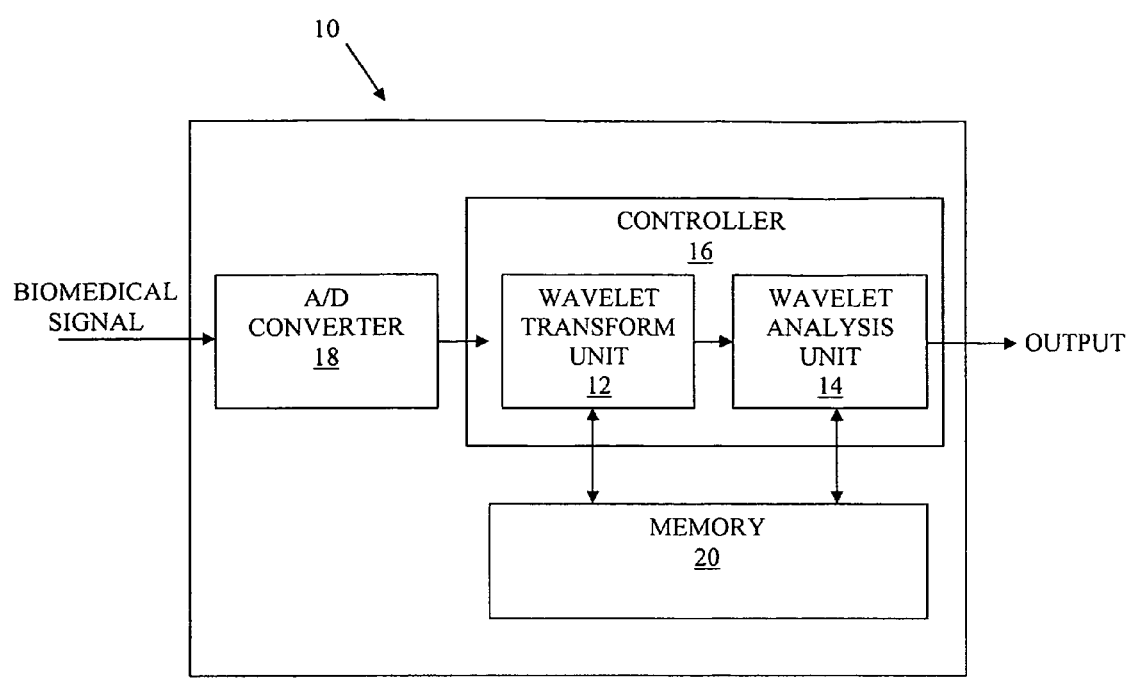
FIG. 1 is an exemplary block diagram of a medical device in accordance with one or more embodiments of the present disclosure.

FIG. 1 is an exemplary block diagram of a medical device 10 according to an embodiment of the invention. Medical device 10 may comprise any of a wide variety of medical devices used to analyze biomedical signals. For example, medical device 10 may comprise an implanted medical device (IMD) that includes various implanted electrodes (not shown) used for sensing the biomedical signals. Alternatively, medical device 10 may comprise an external medical device that uses surface electrodes on a patient's skin to sense the biomedical signals. Also, medical device can be an internal or external device that measure biomedical signals via subcutaneous electrodes. In other cases, medical device 10 may comprise an external device that receives sensed biomedical signals from another device, e.g., via telemetry. In any case, medical device 10 performs signal analysis on biomedical signals using wavelet analysis techniques as described herein.

In general, medical device 10 includes a wavelet transform unit 12 and a wavelet analysis unit 14. In the example illustrated in FIG. 1, wavelet transform unit 12 and a wavelet analysis unit 14 comprise software modules executed on a controller 16. Controller 16 may be implemented with any type of microprocessor, digital signal processor, application specific integrated circuit (ASIC), field programmable gate array (FPGA) or other integrated or discrete logic circuitry programmed or otherwise configured to provide functionality as described herein. Medical device 10 may further include memory 20 to store computer readable instructions that can be executed in controller 16 to realize wavelet transform unit 12 and a wavelet analysis unit 14. For example, memory 20 can comprise random access memory (RAM), read-only memory (ROM), non-volatile random access memory (NVRAM), electrically erasable programmable read-only memory (EEPROM), flash memory, or the like.

Medical device 10 can also include an analog-to-digital (A/D) converter 18 to convert an analog biomedical signal to digital samples that comprise a digital biomedical signal controller 16 receives the digital biomedical signal and invokes wavelet transform unit 12 to transform the biomedical signal to wavelet coefficients and invokes wavelet analysis unit 14 to analyze the wavelet coefficients.

In other embodiments, however, wavelet transform unit 12 and a wavelet analysis unit 14 comprise dedicated hardware or logic that performs the functions described herein. Also, wavelet transform unit 12 and a wavelet analysis unit 14 can be implemented as one or more processors, application specific integrated circuits (ASICs), field programmable gate arrays (FPGAs), various combinations of hardware and software, or the like. Moreover, in some embodiments wavelet transform unit 12 and a wavelet analysis unit 14 can be implemented as analog logic circuits. In that case, the need for controller 16 and A/D converter 18 could be eliminated. However, the illustrated example of FIG. 1, in which wavelet transform unit 12 and wavelet analysis unit 14 comprise software modules executed on controller 16, are relatively easy and cost effective from an implementation standpoint. In that case, the software modules are initially stored in memory 20 and invoked by controller 16 to execute the techniques described herein.

Medical device 10 receives an analog biomedical signal and A/D converter 18 converts the analog biomedical signal to a digital biomedical signal, i.e., a stream of digital samples that represent the biomedical signal. Again, medical device receives the biomedical signal from one or more sensing electrodes of medical device 10, or receives the biomedical signal from another device used to sense the biomedical signals.

Wavelet transform unit 12 receives an biomedical signal (in this case in digital form), and performs wavelet transformation on the biomedical signal to generate a set of wavelet coefficients which collectively include the information in the biomedical signal. For example, wavelet transform unit 12 performs wavelet transformation using mathematical framework similar to that outlined above. In particular, the set of wavelet coefficients can be obtained by scaling and translation of a selected mother wavelet. Wavelet transform unit 12 can comprise a set of dilated impulse response band-pass filters designed to perform the desired wavelet transformation on the biomedical signal. The set of wavelet coefficients generated by wavelet transform unit 12 include numerous wavelet coefficients at various scale factors. The scale factors span from a coarsest scale to a finest scale.

The coarsest scale wavelet coefficients provide the largest overall picture of the biomedical signal, but lack specific details of the biomedical signal. The finest scale wavelet coefficients provide a less complete picture of the biomedical signal, but include more detail. The whole set of wavelet coefficients include wavelet coefficients of a number of different scale factors.

Wavelet analysis unit 14 analyzes the generated wavelet coefficients to identify features of the biomedical signal based on the wavelet coefficients. In accordance with the invention, wavelet analysis unit 14 can distinguish between different biomedical signal features based on whether the certain identifying features appear the set of wavelet coefficients. For example, the output of wavelet analysis unit 14 can comprise an indication of identified features within the biomedical signal, the timing of the identified features within the biomedical signal, an indication of a certain biomedical condition, or a level of severity of a certain biomedical condition.

More specifically, wavelet analysis unit 14 identifies biomedical signal features comprising a chain of conditionally linked wavelet coefficients across various scales of wavelet coefficients starting from the finest scale extending toward the coarsest scale in order to classify the severity of a biomedical condition in the patient.

In one or more embodiments, the wavelet transform unit 12 and the wavelet analysis unit 14 may alternatively be implemented in similar components situated in devices external to the medical device 10 and possibly remote from the patient. In such embodiments, medical device 10 (implantable or externally worn by the patient) transmits sensed biomedical signals to the remove device (e.g., to a remote server) where the wavelet analysis is performed. The results of the wavelet analysis may then be communicated back to at least one of the physician, the patient, or an emergency response (ER) team. In one or more embodiments, medical device 10 may contain sensed biomedical signals stored within its memory, where medical device 10 (implantable or externally worn by the patient) may be interrogated by a programmer configured to perform the wavelet analysis. The programmer may be a device located within a physician's office or at a hospital, where such programmer devices are commonly known to those skilled in the art of implantable or externally worn medical devices. In one or more embodiments, medical device 10 may communicate sensed biomedical signals to another device located within the patient's home or being worn or carried by the patient that is configured to perform the wavelet analysis, where such a device could then be configured to communicate the results of the wavelet analysis back to at least one of the physician, the patient, or an emergency response (ER) team.

Figure 2A:
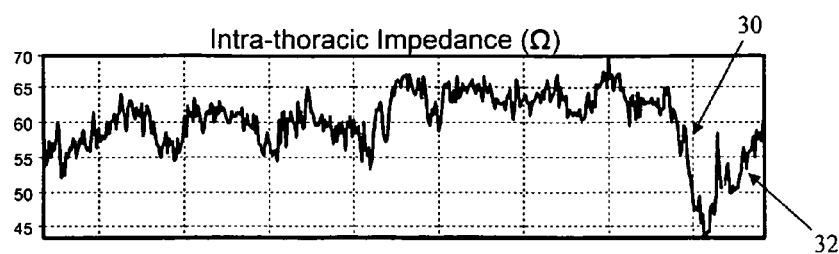
FIGS. 2A-2B are graphs of exemplary intra-thoracic impedance and ePAD values.
Figure 2B:
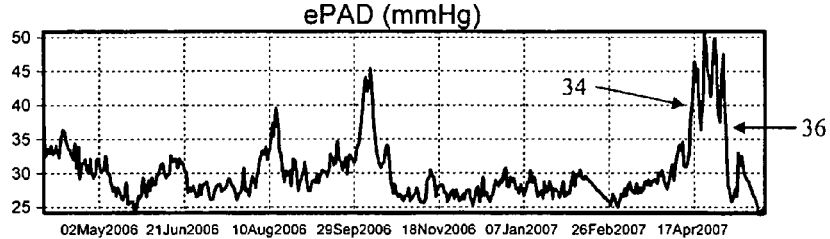

FIG. 2A is a graph of an exemplary intra-thoracic impedance signal in a patient clinically diagnosed with decompensation of heart failure. The X-axis is in units of time (i.e., days and months) and the Y-axis is in units of amplitude (i.e., Ω). FIG. 2B is a graph of an estimated pulmonary arterial pressure (ePAD) signal in the same patient over the same period of time as the signals measured in FIG. 2B. The X-axis of FIG. 2B is also in units of time (i.e., days and months) while the Y-axis is in units of amplitude (i.e., mmHg). Portion 30 of the intra-thoracic impedance signal represents a steep decrease in intra-thoracic impedance due to fluid accumulation in the patient. It can also be seen from FIG. 2B that the fluid accumulation is correlated to a steep increase in ePAD at portion 34 of the ePAD signal. Portion 36 of the ePAD signal shows a decrease and normalizing of the ePAD from fluid drained by the lymphatic system, where a corresponding increase and normalizing of the intra-thoracic impedance can be seen at portion 32 of the intra-thoracic impedance signal. From this, it has been determined that the changes in intra-thoracic impedance and/or ePAD can be used to diagnose or confirm decompensation of heart failure.

Figure 3:
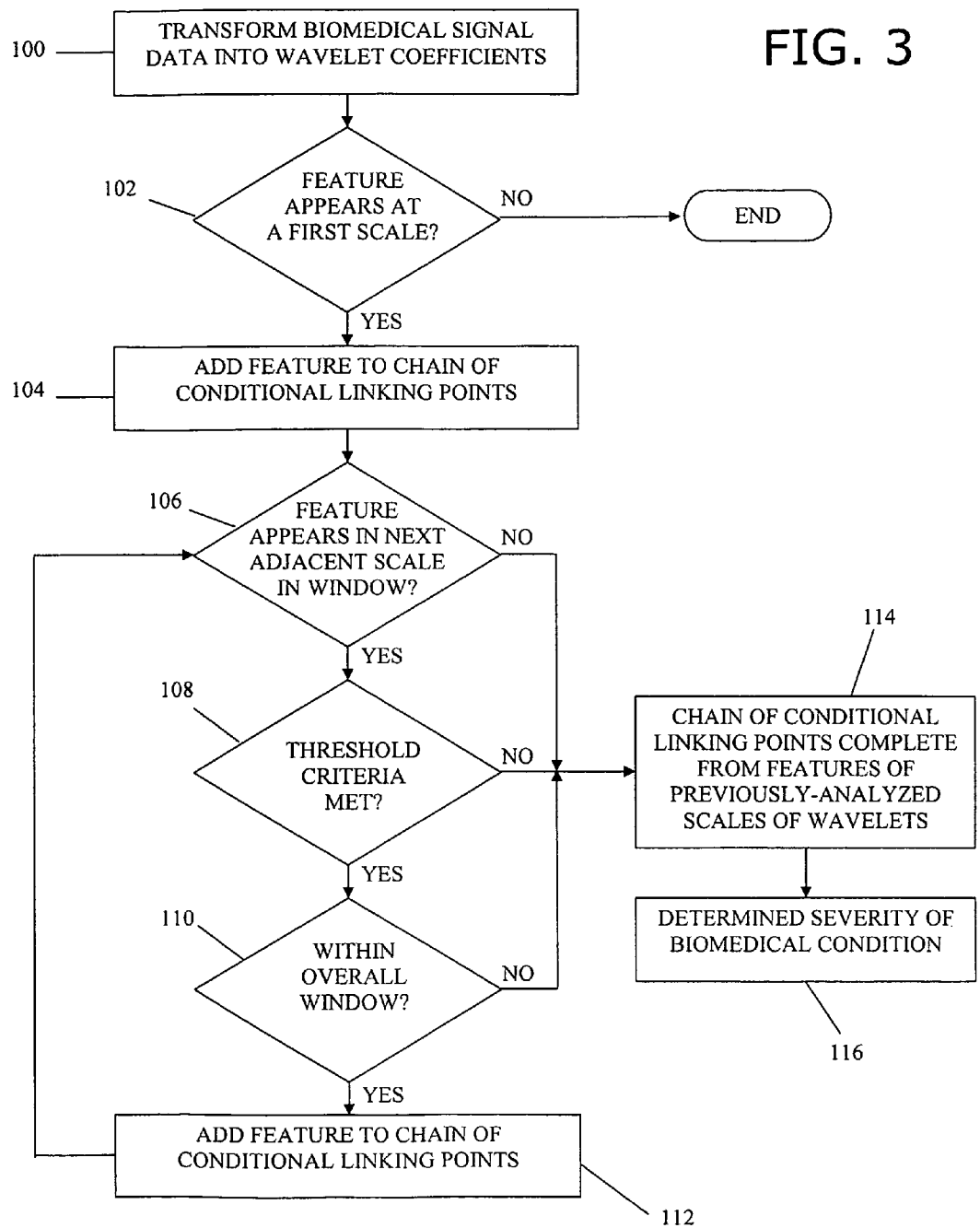
FIG. 3 is an operational flow diagram illustrating a process for classifying the severity of a medical condition detected by a medical device using wavelet based multi-resolution analysis performed on biomedical signals in accordance with one or more embodiments of the present disclosure.

Referring now to FIG. 3, an operation flow diagram is provided for classifying the severity of a medical condition detected by a medical device using wavelet based multi-resolution analysis. In operation 100, biomedical signal data is transformed or otherwise converted into a set of wavelet coefficients, where the set of wavelet coefficients includes a plurality of scales of wavelet coefficients at different resolutions ranging from wavelet coefficients at a finest scale resolution to wavelet coefficients at a coarsest scale resolution. Features of the biomedical signal useful in diagnosing a biomedical condition or parameter (e.g., changes in intra-thoracic impedance, ePAD, etc.) are identified by determining whether corresponding identifying features appear in at least one of the plurality of scales of wavelet coefficients. In one or more embodiments, features of the biomedical signal may further be identified by determining whether the magnitude of certain wavelet coefficients in certain scales of wavelet coefficients exceed predefined threshold values. In one or more embodiments, the particular wavelet transform selected may be chosen to create corresponding characteristics in the wavelet coefficients based on the characteristics of biomedical signal, such that characteristics of the wavelet coefficients can highlight or accentuate characteristics of the biomedical signal or otherwise make characteristics of the biomedical signal more easily identifiable. One manner of creating wavelet coefficients based on a biomedical signal is disclosed in U.S. Pat. No. 7,082,327, the contents of which are hereby incorporated by reference in its entirety.

In one or more embodiments, it is initially determined in operation 102 whether an identified feature appears in wavelet coefficients at a selected first scale. For example, the identifying features appearing in wavelet coefficients at a selected first scale can be selected to be peak wavelet coefficient values appearing within a selected period of time, where peak wavelet coefficient values represent a significant change in the corresponding the biomedical signal. If an identifying feature is determined to be appearing in wavelet coefficients at the selected first scale, it is selected as a base linking point for the conditional linking and added to the set or chain of conditional linking points in operation 104. The wavelet coefficients in an adjacent scale of wavelet coefficients (e.g., coarser or finer scale) is then analyzed in operation 106 to determine whether an identifying feature appears in the next adjacent scale of wavelet coefficients from the base linking point's scale within a first time period window surrounding the base linking point. The first time period window surrounding the base linking point may be predefined or variable defined and further may extend in any direction as long as it contains or surrounds the base linking point.

If an identifying feature is located in the next adjacent scale of wavelet coefficients, it is further determined whether the identified feature appearing in the adjacent scale of wavelet coefficients meets certain threshold criteria in operation 108. In some embodiments, the threshold criteria determination may include determining whether the identifying feature possesses a certain amplitude. If the certain threshold criteria are met, it is determined whether the identified feature is located within an overall time period window in operation 110 for this particular set or chain of conditional linking points. The overall time period window allows only certain periods of time to be analyzed for a particular chain of linking points to ensure that the linking points have a high correlation to each other. If the identifying feature also falls within the overall time period window, the identified feature is selected as a linking point and conditionally linked to the chain of conditional linking points having identified features previously identified to be appearing in the other scales of wavelet coefficients in operation 112. In one or more embodiments, these various operations 106, 108, 110 and 112 are repeated until all desired scales of wavelet coefficients have been analyzed or until a chain of conditional linking points has been completed from a starting base linking point.

The starting base point for the wavelet analysis may begin at any scale of wavelet coefficients. For example, the starting base point may be located at the finest scale so that the scale of wavelet coefficients gradually become coarser as the scales are analyzed, the starting base point may be located at the coarsest scale so that the scale of wavelet coefficients gradually become finer as the scales are analyzed, or the starting base point may be located at an intermediate scale of wavelet coefficients so that the scale of wavelet coefficients are analyzed in either a gradually finer direction, a gradually coarser direction or a combination of both directions.

In one or more embodiments, the chain of conditional linking points is determined to be complete in operation 114 if either i) an identified feature is not located in the next adjacent scale of wavelet coefficients, ii) the certain threshold criteria are not satisfied for an identified feature in the next adjacent scale of wavelet coefficients, or iii) the overall time period window condition is not satisfied for an identified feature in the next adjacent scale of wavelet coefficients. The identified features in each of the plurality of scales of wavelet coefficients that are conditionally linked together can then be used to determine or classify a degree of severity of a biomedical condition by correlating identifying features of the wavelet coefficients to identifying features of the biomedical signal. In one or more embodiments, once the chain of conditional linking points has been determined, the degree of severity of the biomedical condition can be classified in operation 116 based on the number of linking points in the chain of conditional linking points. For example, one chain of conditional linking points having a greater number of linking points than another chain of conditional linking points may be classified to be associated with a more severe condition (i.e., the more linking points the more severe the condition).

In one or more embodiments, the degree of severity of the biomedical condition can additionally or alternatively be classified based on whether the magnitude of certain wavelet coefficients in certain scales of wavelet coefficients exceed predefined threshold values. In such embodiments, a biomedical condition may still be classified as a severe condition based on the magnitude or amplitude of a specific wavelet coefficient even if a large number of conditional linking points are not present in the chain of conditional linking points.

In some embodiments, the classified degree of severity of the biomedical condition can be associated with certain categories of classifications, such as but not limited to a color-coded classification system (e.g., code red, code orange, code green, etc.) or a numerical classification system (e.g., level 10, level 9, etc.), or any other type of category of classification. In one or more embodiments, an alert can be generated to at least one of the patient, a physician, and an emergency response team when certain degrees of severity of the biomedical condition are identified to exist. The particular type of alert generated and the parties receiving the alert can vary depending upon the classified severity of the biomedical condition. In some embodiments, the alert may include generating instructions to the patient, a physician, a clinician or an ER individual to take certain actions for treating the diagnosed condition. For example, the patient can be alerted of the diagnosed medical condition and notified with instructions to take certain therapeutic actions (e.g., taking aspirin, nitrates, fluids, diuretics, go to the emergency room, etc.). Still further, the instructions can instruct the patient, emergency response personnel and/or bystanders to take appropriate actions to treat the detected condition, where such instructions could be part of a bidirectional communication that occurs with paramedics/physicians that were alerted of the detected condition. In some embodiments, the possible automated responses include providing instructions for collecting additional biomedical signal data, where this additional information can be used to further diagnose additional aspects of the medical condition.

Referring now to FIGS. 4-8, various embodiments of the system and method for classifying the severity of a medical condition detected by a medical device using wavelet based multi-resolution analysis described herein are shown being extending to the classification of decompensation of heart failure in a patient in which intra-thoracic impedance values are used as the biomedical signal data. In this manner, the severity of heart decompensation in a patient can be easily detected and classified by wavelet transforming intra-thoracic impedance values into multi-resolution scales of wavelet coefficients and conditionally linking the wavelet coefficient peaks. The representative example set forth in the following description associated with FIGS. 4-8 is being set forth to assist in the understanding of the application of the present system and methods to a real-world diagnosis of a biomedical condition of patient without limiting the present system and methods to this one example.

Figure 4:
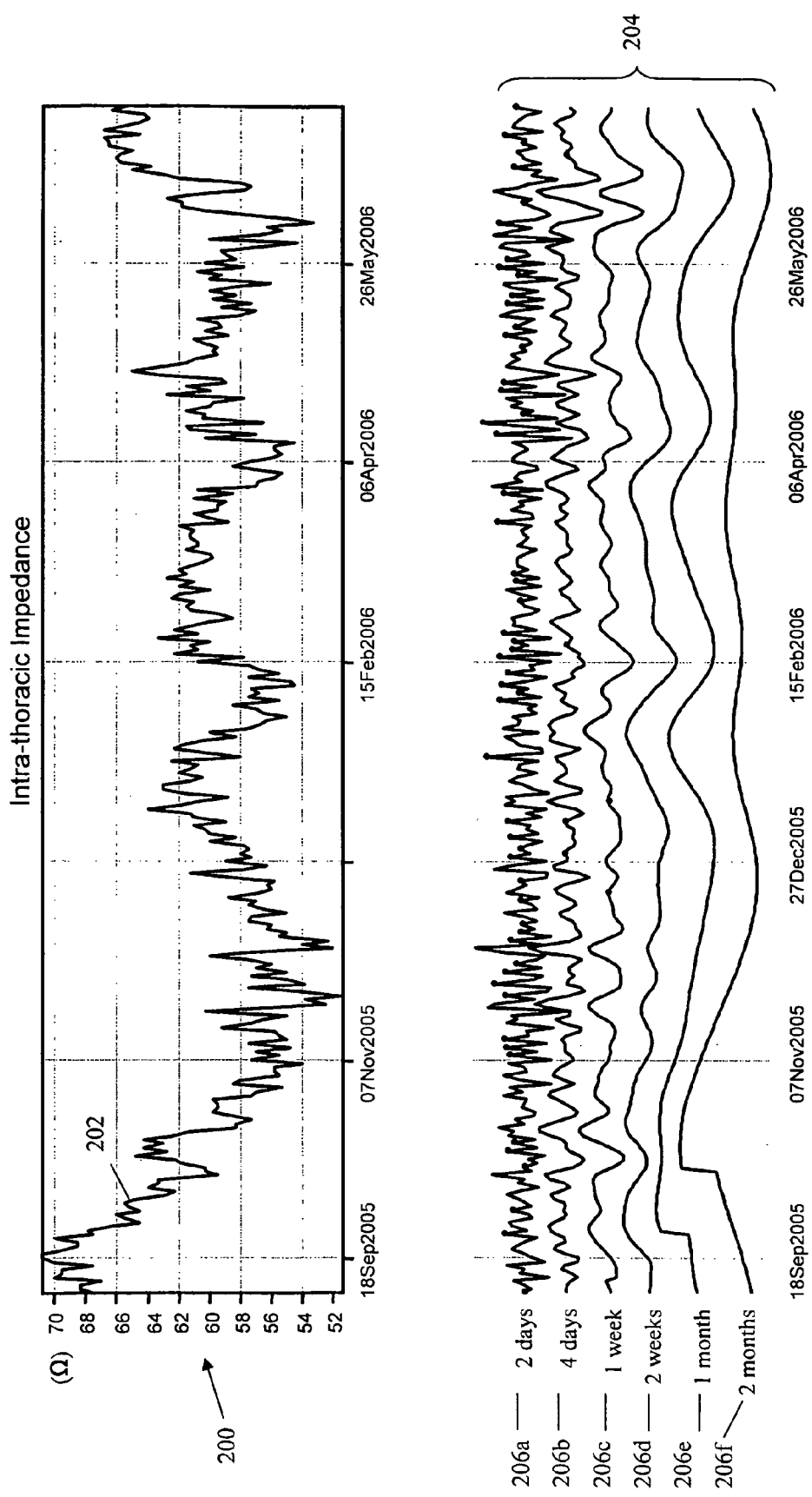
FIGS. 4 and 5 are graphical illustrations showing an exemplary intra-thoracic impedance and its corresponding set of wavelet coefficients in accordance with one or more embodiments of the present disclosure.

FIG. 4 includes a graph 200 including an exemplary intra-thoracic impedance signal 202 and its associated transformed set of wavelet coefficients 204 that includes a plurality of scales of wavelet coefficients 206a-206f at different resolutions ranging from wavelet coefficients at a finest scale resolution (i.e., 2 days) to wavelet coefficients at a coarsest scale resolution (i.e., 2 months). In some embodiments, the scales can be selected to double for each adjacent coarser scale of resolution for simplicity of the algorithm and efficiency of power usage in the medical device 10.

Figure 5:
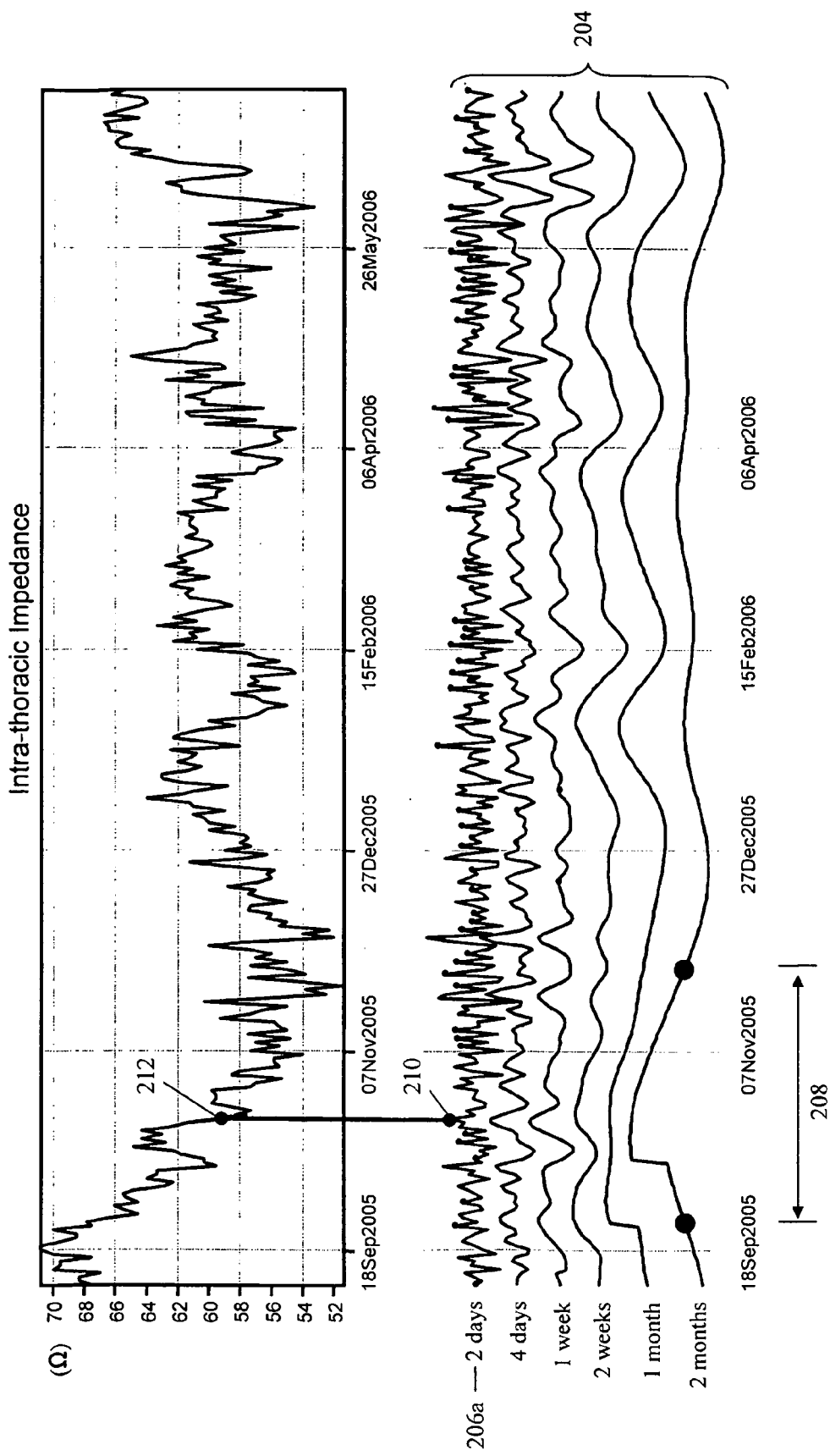

With reference to FIG. 5, it can be seen that during an overall time period 208 that the intra-thoracic impedance signal generally decreases over time, which can be easily detected through analysis of the set of wavelet coefficients 204. Beginning at the finest scale 206a representing a scale of 2 days in this example, a peak wavelet coefficient value 210 is identified within a selected overall time period 208. The peak wavelet coefficient value 210 corresponds to a significant decrease in the intra-thoracic impedance over a short period of time at portion 212 of the intra-thoracic impedance signal 202. This peak wavelet coefficient value 210 is selected as the base linking point for the chain of conditional linking points within the overall time period 208.

With reference to FIG. 6, the wavelet coefficients in the next adjacent coarser scale of wavelet coefficients 206b are then analyzed within a time period window 214 surrounding the base linking point 210 to determine whether a peak wavelet coefficient value appears in the next adjacent coarser scale of wavelet coefficients 206b (e.g., 4 days in this example). Peak wavelet coefficient value 216 is identified. It is then determined whether peak wavelet coefficient value 216 meets a certain amplitude threshold and whether it is located within overall time period window 208. If both of these conditions are satisfied, peak wavelet coefficient value 216 is selected as a linking point and conditionally linked to the chain of conditional linking points 220, so that the chain 220 now includes two linking points 210 and 216.

With reference to FIG. 7, the wavelet coefficients in the next adjacent coarser scale of wavelet coefficients 206c are then analyzed within a time period window 222 surrounding the last linking point 216 to be added to the chain of linking points 220 to determine whether a peak wavelet coefficient value appears in the next adjacent coarser scale of wavelet coefficients 206c (e.g., 1 week scale in this example). Peak wavelet coefficient value 224 is identified. It is then determined whether peak wavelet coefficient value 224 meets a certain amplitude threshold and whether it is located within overall time period window 208. If both of these conditions are satisfied, peak wavelet coefficient value 224 is selected as a linking point and conditionally linked to the chain of conditional linking points 220, so that the chain 220 now includes two linking points 210, 216 and 224.

Figure 8:
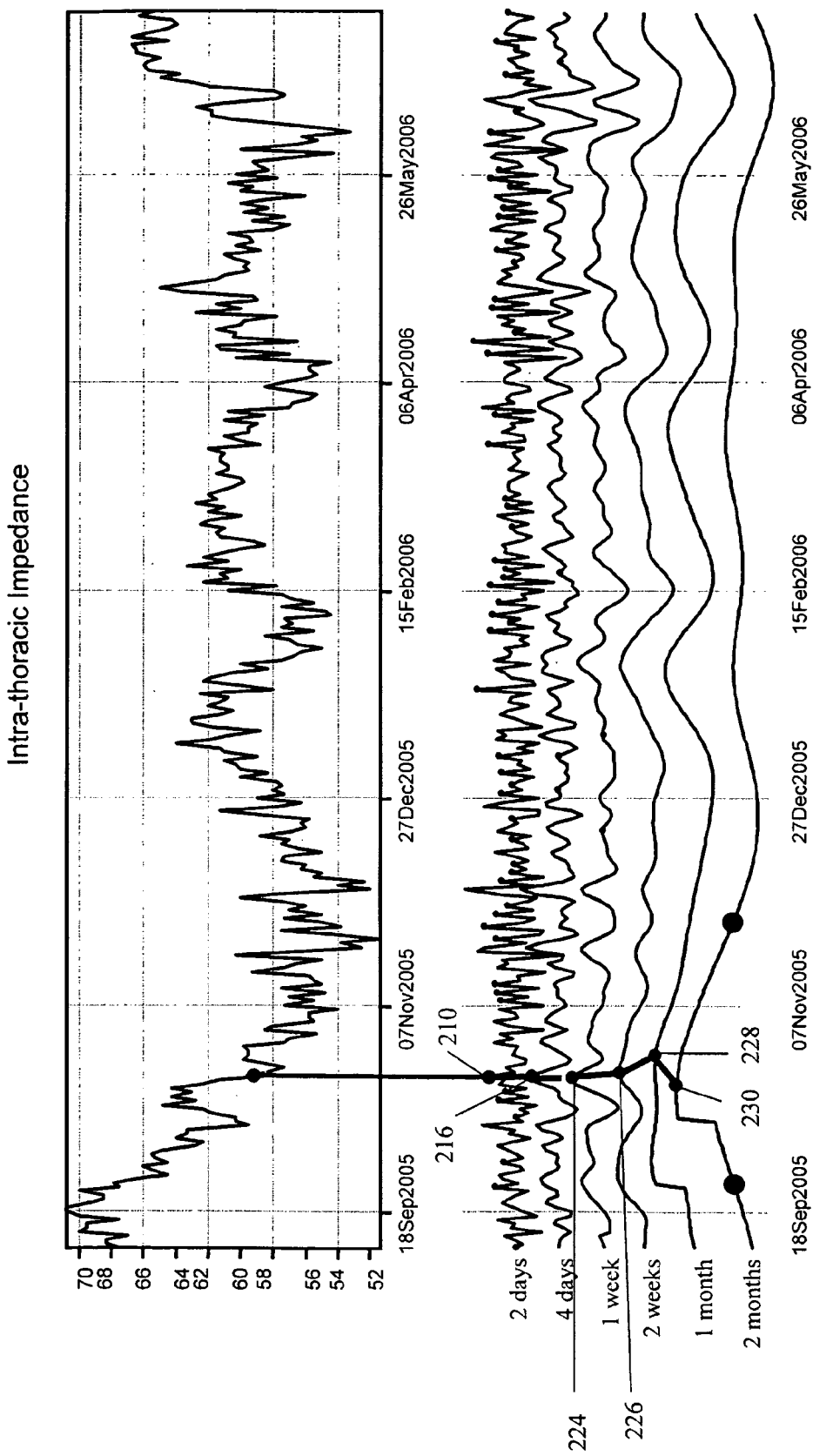
FIG. 8 is a further graphical illustration showing the exemplary intra-thoracic impedance and corresponding set of wavelet coefficients of FIGS. 4-7 in accordance with one or more embodiments of the present disclosure.

This analysis is repeated for the remaining scales 206d-206f through the coarsest scale 206f (i.e., 2 months in this example) until the entire set of scales of wavelet coefficients 206a-206f has been analyzed to generate a completed chain of linking points 220, as illustrated in FIG. 8. Alternatively, the chain of linking points 220 will be completed prior to the coarsest scale 206f if any of the above-described tests and conditions for linking points are not satisfied in any given scale of wavelet coefficients. In this example, it can be seen that the completed chain of linking points 220 includes six linking points 210, 216 and 224, 226, 228 and 230. Once the chain of conditional linking points 220 has been completely determined, the degree of severity of the biomedical condition can be classified based on the number of linking points (i.e., six in this example) in the chain of conditional linking points 220.

Figure 9:
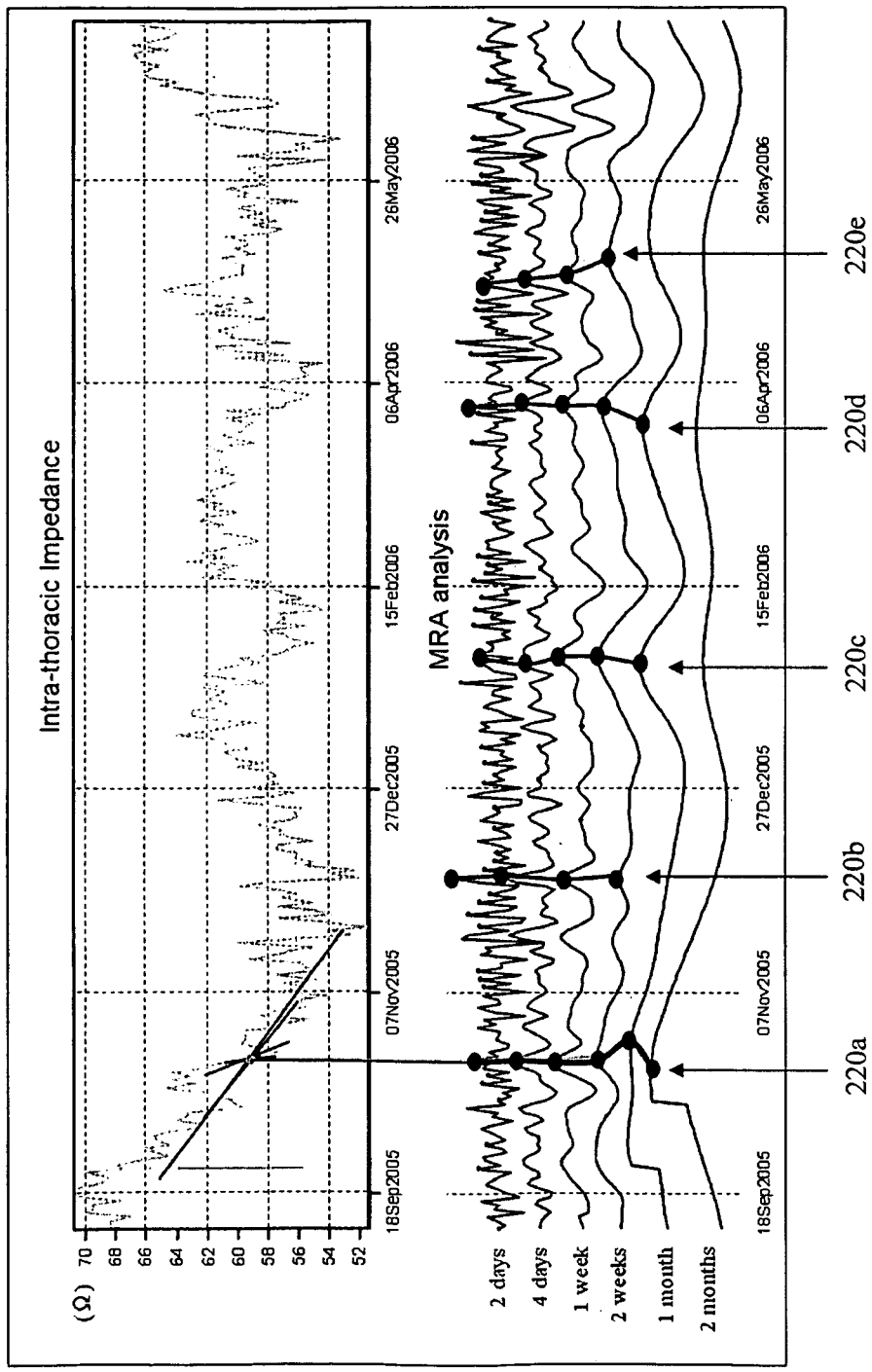
FIG. 9 is a graphical illustration showing an exemplary intra-thoracic impedance and its corresponding set of wavelet coefficients having multiple chains of linking points in accordance with one or more embodiments of the present disclosure.

The system and methods of the embodiments described herein can be repeatedly performed at various points in time to generate chains of conditional linking points 220 at different points in time, as illustrated as chains of conditional linking points 220a-220e in FIG. 9. It can be seen from chains of conditional linking points 220a-220e in FIG. 9 have varying lengths (i.e., varying numbers of linking points in each chain), where it can likewise be seen that the chains of conditional linking points 220a-220e having the greatest lengths or numbers of linking points are associated with longer periods of decreasing intra-thoracic impedance values. Since a decrease in intra-thoracic impedance measurements is indicative of increases in fluid content and the accumulation of fluid can indicate decompensation of heart failure in a patient, the severity of the diagnosed decompensation in the patient can be classified based upon the number of linking points in each chain of conditional linking points 220a-220e. In this example, chain of conditional linking points 220a having six linking points would be classified as a more severe decompensation than chain of conditional linking points 220b having only four linking points. It can thus be seen that the present system and methods provide a simple, efficient mechanism for diagnosing and classifying the severity of a medical condition using a medical device by applying wavelet based multi-resolution analysis.

While the system and method have been described in terms of what are presently considered to be specific embodiments, the disclosure need not be limited to the disclosed embodiments. It is intended to cover various modifications and similar arrangements included within the spirit and scope of the claims, the scope of which should be accorded the broadest interpretation so as to encompass all such modifications and similar structures. The present disclosure includes any and all embodiments of the following claims.

The invention claimed is:

1. A method comprising:
 converting biomedical signal data into a set of wavelet coefficients, the set of wavelet coefficients including a plurality of scales of wavelet coefficients extending from wavelet coefficients at a fine scale to wavelet coefficients at a coarse scale;

identifying features of the biomedical signal data based on whether corresponding identifying features appear in at least one of the plurality of scales of wavelet coefficients;

conditionally linking identified features in each of the plurality of scales of wavelet coefficients to determine a degree of severity of a biomedical condition based on the identified features of the biomedical signal data.

2. The method of claim 1, further comprising:
determining whether an identified feature appears in wavelet coefficients at a first selected scale;
selecting the identified featured appearing in wavelet coefficients at the first selected scale as a base point for the conditional linking.

3. The method of claim 2, further comprising determining whether an identified feature appears in an adjacent scale of wavelet coefficients from the base point scale within a first time period window surrounding the base point.

4. The method of claim 3, further comprising:
determining whether the identified feature appearing in the adjacent scale of wavelet coefficients meets certain threshold criteria; and
if the certain threshold criteria are met, identifying the identified feature as a linking point and conditionally linking the identified feature appearing in the adjacent scale of wavelet coefficients to the base point to represent a chain of conditional linking points.

5. The method of claim 4, further comprising repeatedly performing the following operations until a chain of conditional linking points has been completed without break between consecutive scales of wavelet coefficients:
determining whether an identified feature appears in a next adjacent scale of wavelet coefficients from a linking point that was last added to the chain of conditional linking points in a time period window surrounding the last added linking point;
if an identified feature is located in the next adjacent scale of wavelet coefficients,
determining whether the identified feature appearing in the next adjacent scale of wavelet coefficients meets certain threshold criteria, and
determining whether the identified feature appearing in the next adjacent scale of wavelet coefficients is located within an overall time period window for the entire chain of conditional linking points; and
if the certain threshold criteria and overall time period window conditions are satisfied, identifying the identified feature as a linking point and conditionally linking the identified feature appearing in the next adjacent scale of wavelet coefficients to the chain of conditional linking points having identified features appearing in the other scales of wavelet coefficients.

6. The method of claim 5, wherein the chain of conditional linking points is complete if either an identified feature is not located in the next adjacent scale of wavelet coefficients, the certain threshold criteria are not satisfied for an identified feature in the next adjacent scale of wavelet coefficients, or the overall time period window condition is not satisfied for an identified feature in the next adjacent scale of wavelet coefficients.

7. The method of claim 5, further comprising determining the degree of severity of the biomedical condition based on the number of linking points in the chain of conditional linking points.

8. The method of claim 1, further comprising generating an alert to at least one of the patient, a physician, and an emergency response team when certain degrees of severity of the biomedical condition are identified.

9. The method of claim 1, wherein the biomedical signal data includes at least one of intra-thoracic impedance and intracardiac pressure values, further wherein the biomedical condition includes decompensation in heart failure in a patient.

10. A medical device, comprising:
a wavelet coefficient transform unit configured to convert biomedical signal data into a set of wavelet coefficients, the set of wavelet coefficients including a plurality of scales of wavelet coefficients extending from wavelet coefficients at a fine scale to wavelet coefficients at a coarse scale;
a wavelet analysis unit configured to identify features of the biomedical signal data based on whether corresponding identifying features appear in at least one of the plurality of scales of wavelet coefficients;
the wavelet analysis unit further configured to conditionally link features identified in the plurality of scales of wavelet coefficients to determine a degree of severity of a biomedical condition based on the identified features of the biomedical signal data.

11. The medical device of claim 10, wherein the wavelet analysis unit is further configured to:
determine whether an identified feature appears in wavelet coefficients at a first selected scale; and
select the identified featured appearing in wavelet coefficients at the first selected scale as a base point for the conditional linking.

12. The medical device of claim 11, wherein the wavelet analysis unit is further configured to determine whether an identified feature appears in an adjacent scale of wavelet coefficients from the base point scale within a first time period window surrounding the base point.

13. The medical device of claim 12, wherein the wavelet analysis unit is further configured to:
determine whether the identified feature appearing in the adjacent scale of wavelet coefficients meets certain threshold criteria; and
if the certain threshold criteria are met, identify the identified feature as a linking point and conditionally link the identified feature appearing in the adjacent scale of wavelet coefficients to the base point to represent a chain of conditional linking points.

14. The medical device of claim 13, wherein the wavelet analysis unit is further configured to repeatedly perform the following operations until a chain of conditional linking points has been completed without break between consecutive scales of wavelet coefficients:
determine whether an identified feature appears in a next adjacent scale of wavelet coefficients from a linking point that was last added to the chain of conditional linking points in a time period window surrounding the last added linking point;
if an identified feature is located in the next adjacent scale of wavelet coefficients,
determining whether the identified feature appearing in the next adjacent scale of wavelet coefficients meets certain threshold criteria, and
determining whether the identified feature appearing in the next adjacent scale of wavelet coefficients is located within an overall time period window for the entire chain of conditional linking points; and
if the certain threshold criteria and overall time period window conditions are satisfied, identifying the identified feature as a linking point and conditionally linking the identified feature appearing in the next adjacent scale of wavelet coefficients to the chain of conditional linking points having identified features appearing in the other scales of wavelet coefficients.

15. The medical device of claim 14, wherein the chain of conditional linking points is complete if either an identified feature is not located in the next adjacent scale of wavelet coefficients, the certain threshold criteria are not satisfied for an identified feature in the next adjacent scale of wavelet coefficients, or the overall time period window condition is not satisfied for an identified feature in the next adjacent scale of wavelet coefficients.

16. The medical device of claim 14, wherein the wavelet analysis unit is further configured to determine the degree of severity of the biomedical condition based on the number of linking points in the chain of conditional linking points.

17. The medical device of claim 10, further comprising an alert generation unit to generate an alert to at least one of the patient, a physician, and an emergency response team when certain degrees of severity of the biomedical condition are identified.

18. The medical device of claim 10, wherein the biomedical signal data includes at least one of intra-thoracic impedance and intracardiac pressure values, further wherein the biomedical condition includes decompensation in heart failure in a patient.

* * * * *